United States Patent [19]

Crawford et al.

[11] Patent Number: 5,232,845
[45] Date of Patent: Aug. 3, 1993

[54] BACTERIAL EXTRACELLULAR LIGNIN PEROXIDASE

[75] Inventors: Donald L. Crawford, Moscow, Id.; Muralidhara Ramachandra, Wilmington, Del.

[73] Assignee: Idaho Research Foundation Inc., Moscow, Id.

[21] Appl. No.: 422,023

[22] Filed: Oct. 16, 1989

Related U.S. Application Data

[63] Continuation-in-part of Ser. No. 277,802, Nov. 30, 1988, Pat. No. 5,200,338.

[51] Int. Cl.$^5$ .................... C12N 15/00; C12N 15/53; C12N 15/74
[52] U.S. Cl. .................... 435/189; 435/64.1; 435/172.3; 435/252.35; 435/320.1; 536/23.2; 935/14; 935/29; 935/75
[58] Field of Search ............... 435/69.1–69.9, 435/172.1–172.3, 252.3–252.35, 320.1, 189, 192; 536/27

[56] References Cited

U.S. PATENT DOCUMENTS 4,713,336 12/1987 Srinivasan et al. ............... 435/155

FOREIGN PATENT DOCUMENTS 0261080 3/1988 European Pat. Off.
86/02094 4/1986 PCT Int'l Appl.

OTHER PUBLICATIONS

F. Rafii et al., *Appl. Environ. Microbiol.*, 54(6):1334–1340 (1988).
M. Ramachandra et al., *Appl. Environ. Microbiol.*, 54(12):3057–3063 (1988).
Tien and Kirk in *Science* (1983) 221:661–663.
D. Crawford in *Applied and Environmental Microbiology* (1978) 35:1041–1045.
Crawford, et al., *Applied and Environmental Microbiology* (1983) 45:898–904.
Mason et al., *Applied Microbiology and Biotechnology* (1988) 28:276–280.
Ramachandra, et al., *Applied and Environmental Microbiology* (1987) 53:2754–2760.
Tien et al., *Nature (1987) 326:520–523*.
Rafael Vicuna in *Enzyme Microb. Technol.* (1988) 10:646–655.
Tien, et al., *Proc. Natl. Acad. Sci. USA* (1984) 81:2280–2284.
Kumoda, et al., *Agric. Biol. Chem.* (1989) 53(10) 2757–2761.
Zhang, et al., *Biochem. Biophys. Res Comm.* (1986) 137:649–656.
Akhi, T. P., et al., 1989, Applied and Environmental Microbiology, 55(5): 1165–1168.
McCarthy, A. J., 1986, Applied Microbiology and Biotechnology 24: 347–352.
Katz, E., et al., 1983, Journal of General Microbiology, 129: 2703–2714.
Chet, I., et al., 1985, Microbios Lettters, 29(113): 37–43.

*Primary Examiner*—Robert A. Wax
*Assistant Examiner*—William W. Moore
*Attorney, Agent, or Firm*—Cooley Godward Castro Huddleson & Tatum

[57] ABSTRACT

DNA constructs are provided for the production of Streptomyces lignin peroxidase. The enzyme finds use in the degradation of lignin and oxidation of organic substrates.

16 Claims, No Drawings

BACTERIAL EXTRACELLULAR LIGNIN PEROXIDASE

The research was supported in part by the United States Environmental Protection Agency under Research Contract CR-815300-01-0 and United States Department of Energy Grant DE-FG786ER13586, and National Science Foundation Grant VCS-8807000. The United States Government may have rights in this invention.

CROSS-REFERENCE TO RELATED APPLICATIONS

This application is a continuation-in-part of application Ser. No. 277,802, filed Nov. 30, 1988, now U.S. Pat. No. 5,200,338.

INTRODUCTION

1. Technical Field

The field of the subject invention concerns the expression of lignin peroxidase in a native or heterologous host.

2. Background

Lignin is a by-product of the production of paper and tends to be an intransigent material with low economic value. Furthermore, there are substantial costs associated with the removal of lignin in the pulping of wood.

Organisms are known which are capable of oxidatively depolymerizing lignin as the organism degrades the cellulose and hemi-cellulose components of plant residues. The depolymerization reactions produce a modified water-soluble acid precipitable polymeric lignin as a major lignin degradation product. Extra-cellular lignin peroxidases are thought to catalyze the initial catabolism of lignin. The enzymes used by the organism for water-solubilizing lignin could be useful in commercial delignification processes. Therefore, there is substantial interest in the development of enzymatic compositions which may be used in commercial processes for the efficient and economical removal of lignin.

Relevant Literature

A lignocellulose-induced extra-cellular lignin peroxidase (bacterial lignin peroxidase ALip-P3) in *S. viridosporus* T7A is reported by Ramachandra et al., *Appl. Environ. Microbiol.* 1988, 54:3057–3063. See also, Ramachandra et al., *Appl. Environ. Microbiol.* 1987, 53:2754–2760.

Other lignin-depolymerizing actinomycetes have been described: *Thermomonsopora mesophilia*, McCarthy et al. 1986, *Appl. Environ. Microbiol. Biotechnol.*, 24:347–352; McCarthy, 1987, *FEMS Microbiol. Rev.*, 46:145–163; *Streptomyces badius* 252, Phelan et al., *Can. J. Microbiol.* 1979, 25:1270–1276; Borgmeyer and Crawford, *Appl. Environ. Microbiol.* 1985, 49:273–278; *S. Viridosporus*, Adhi et al., 1989, ibid., 55:1165–1168. See also Giroux et al., 1988, ibid, 54:3064–3070 and Ball et al., ibid, 55:1642–1644.

SUMMARY OF THE INVENTION

DNA sequences and methods employing DNA sequences both for identifying lignin peroxidase and for expressing lignin peroxidase by recombinant DNA technology are provided. The lignin peroxidase are capable of degrading lignocellulose and the lignin peroxidase gene can be transformed into hosts to enhance lignocellulose degrading activity.

DESCRIPTION OF SPECIFIC EMBODIMENTS

DNA sequences, DNA constructs, vectors and transformed hosts are provided for the expression of lignin peroxidase, where the enzyme and host capable of expressing the enzyme may be used for the degradation of lignin and lignocellulose.

Lignin peroxidases are found in a number of Streptomyces species including *S. viridosporus, S. cyaneus, badius,* and other actinomycetes, such as *Thermomonosopora mesophilia*. The enzymes are characterized by being involved with the initial catabolism of lignin, being lignocellulose-induced, extracellular, catalyzing a carbon-carbon bond cleavage in the side chains in phenolic and non-phenolic lignin substructure models, requiring the presence of hydrogen peroxide or a hydrogen peroxide source and oxidizing polymeric lignin. Induction of production of the subject enzymes may also be induced by lignin, cellulose, larch wood xylan or polymeric lignin degradation intermediates. The peroxidase is a heme protein with broad substrate specificity. Besides lignin and lignin-like products, the subject enzymes will oxidize other phenolics, including chlorinated aromatic compounds. The enzymes has a molecular weight of about 32,000–34,000 daltons, but may be composed of multiple subunits.

The enzyme shows oxidative activity at a pH range of about 4–8, and at a temperature of about 25°–50° C. Acidic pH conditions are preferred (optimum pH 5.5–5.6).

The DNA encoding this subject enzyme may be isolated by preparing a library from a lignin peroxidase producing host. The resulting clones are then transformed into a strain of the same or related species that has a negative background for lignin peroxidase activity. The resulting transformants may then be screened using a dye, e.g., blue polymeric Poly B-411, which is a substrate for ligninases. Colonies with clear halos are picked for further investigation. The clones may be further screened with additional dyes, including a variety of phenolic dyes, used by themselves or in conjunction with 4-aminoantipyrine.

In addition, the clones may be further screened to establish the ability to provide lignocellulose degradation. By growing the transformed hosts on a lignocellulose source and comparing the amount of degradation of the lignocellulose as compared to the untransformed parent, the presence of the gene encoding the lignin peroxidase can be established.

The library will usually contain DNA fragments ranging from about 2 to 10 kb, more usually from about 3 to 8 kb. These fragments may be readily excised from the library, once one or more clones have been identified as comprising the lignin peroxidase gene. The fragment may be further reduced in size by employing various nucleases, such as restriction endonucleases, mung bean nuclease, or the like. The resulting fragments may be further screened as described above. Fragments may be tailored by using exonucleases for removing nucleotides at one or both ends of the fragment. Messenger RNA may be obtained from the transformed host and subtracted with cDNA made from the untransformed host in order to enrich for the lignin peroxidase message. The DNA fragment containing the lignin peroxidase may then be hybridized with the mRNA composition having the enriched lignin peroxidase message, so as to define the message, which may then be used to produce cDNA for the gene encoding the lignin peroxidase. In addition, the cDNA for the lignin peroxidase may be used to identify the 5' flanking region which includes the inducible promoter.

The DNA may be used in a variety of constructs. The fragment containing the genomic gene may be used directly by insertion into an appropriate vector for transformation of a competent host. The vector may provide for stable extrachromosomal maintenance or for integration into the genome of the host. One can employ a host which provides the necessary heme prosthetic group to produce the holoenzyme or may provide a host which does not provide the heme prosthetic group resulting in the apoenzyme. As appropriate, the heme prosthetic group may be provided extrinsically, if desired.

The genomic fragment may be further tailored in a variety of ways, as described above, where the 5' flanking region may be removed from the coding region of the gene and replaced with a promoter functional in the transformed host. The promoter may be constitutive or inducible, depending upon the purpose of the transformation. For example, if the organism is to be used for degrading lignocellulose, it may be desirable to have an inducible promoter which responds to the presence of lignocellulose. By contrast, where one wishes only to produce the enzyme and use it extracellularly, a constitutive strong promoter would be desirable. In some instances, it may be desirable to amplify the gene, by integrating the gene into the host genome in conjunction with an amplifying gene, such as DHFR, metallothionein or the like.

A wide variety of expression vectors exist or may be readily prepared for numerous hosts. Vectors are usually characterized by having a replication system which is functional for cloning in a cloning vector, e.g., E. coli, a replication system for the transformed host for expression of the gene, one or more markers for selection in the cloning host and the expression host, one or more polylinkers, particularly where a polylinker is flanked 5' by a promoter region and 3' by a termination region (5'-3' in the direction of transcription).

The markers may provide for stress resistance, such as to antibiotics, heavy metals or other biocide, complementation to an auxotrophic host, virus resistance, or the like.

The various fragments may be joined together by ligation and may be manipulated by primer repair, in vitro mutagenesis, endonuclease restriction, resection, tailing, or the like.

Of particular interest are vectors having a functional replication system capable of stable maintenance in prokaryotes, particularly actinomycetes, more particularly Streptomyces, although other prokaryotes may te of interest, such as E. coli, B. subtilis, B. thermophilous, or even eukaryotic microorganisms, e.g., fungi. Any promoter which is employed will be functional in the expression host. As already indicated, the native promoter may be employed or may be replaced with a different promoter, depending upon the purpose for expression, the particular host, and the like. An illustrative promoter is the β-galactosidase promoter.

Transformation of the host may be achieved in accordance with conventional ways. With actinomycetes, transformation can be achieved by preparing protoplasts and transforming the protoplasts with a fusogen, e.g., polyethylene glycol, and then regenerating the Streptomyces cells and screening for the presence of the DNA construct. Clones positive for the presence of the DNA construct may then be screened for expression of lignin peroxidase as described above.

Once the host has been transformed, it may be used for the production of the enzyme, which may be isolated in accordance with known ways. Where the enzyme is secreted, it may be isolated from the supernatant by extraction, precipitation, etc., and, if desired, further purified using an affinity column or other technique. Where the enzyme is localized to the cytosol, the cells may be lysed, the lysate freed of the debris and the lignin peroxidase isolated by extraction, protein precipitation, chromatography, or the like.

The transformant or the enzyme may be used for the degradation of lignin or for oxidation of phenolic or other susceptible compounds. The genes may be used to enhance a host already competent in lignin degradation, to impart to a host the partial or complete capability for lignin degradation, where the subject gene may be used by itself or in conjunction with genes for other enzymes involved with lignin degradation, or for the production of the enzyme which may find use in industrial processes as an oxidation catalyst. The enzyme may be obtained in a concentration in the range of about 0.4–0.8 U ml$^{-1}$ (U as defined in the Experimental section) and may be further concentrated and purified.

The following examples are offered by way of illustration and not by way of limitation.

EXAMPLES

Materials and Methods

Microorganisms

*Streptomyces viridosporus* T7A (ATCC 39115) is a lignin-solubilizing actinomycete (Crawford et al. 1983, *Appl. Environ. Microbiol.* 45:898–904) originally isolated from Idaho soil (D. L. Sindin, M.S. thesis, Univ. Idaho 1979). *Streptomyces lividans* TK64, TK23, and TK 24 were kindly supplied by D. A. Hopwood (John Innes Institute, Norwich, England). Strain TK64 is a proline auxotroph and is resistant to streptomycin (chromosomally encoded), while nonauxotrophic strains TK23 and TK24 express chromosomally encoded resistance to spectinomycin and streptomycin, respectively (Hopwood et al., 1985, Genetic manipulation of Streptomyces: A Laboratory Manual, John Innes Foundation, Norwich, UK). Stock cultures were maintained on yeast extract-malt extract-glucose agar (YEMED) (Ramachandra et al., 1987, supra). Spores from stock slants were used as inoculum in all experiments. Organic medium components were obtained from Difco Laboratories (Detroit, Mich.).

Plasmic Vector

The 5.8 kb plasmid pIJ702 (Katz et al. 1983, *J. Gen. Microbiol* 129:2703–2714) was kindly supplied in *Streptomyces lividans* TK150 by D. A. Hopwood (John Innes Institute, Norwich, England). The plasmid carries thiostrepton resistance (tsr$^r$) as a selectable marker and tyrosinase (mel+) which is insertionally inactivated during cloning. Stocks of TK150 were maintained on YEMED agar slants containing 50 mµg ml$^{-1}$ of thiostrepton.

Plasmid Isolation

For isolation of pJI702, cultures were grown in yeast extract-malt extract-sucrose (YEME) medium with thiostrepton (50 µg ml$^{-1}$) and 5 mM MgCl$_2$. Plasmid DNA was isolated by the alkaline sodium dodecyl sulfate procedure as described by Hopwood et al. 1985, supra, with some modification (Maniatis et al., 1982, Molecular Cloning: A Laboratory Manual CSHL, Cold Spring Harbor, N.Y.). The full procedure has been previously described (Rafii and Crawford 1988, *Appl. Environ. Microbiol.* 54:1334–1340).

DNA Characterizations

Restriction enzyme digestions, agarose gel electrophoresis, DNA labeling with biotin, Southern blot hybridizations, and colony hybridizations were carried out as previously described (Maniatis et al., 1982, supra; Rafii and Crawford 1988, supra.

Sources of Enzymes, Antibiotic, and Chemicals

Restriction enzymes were purchased from Bethesda Research Laboratories (BRL; Bethesda, Md.), and digestions were carried out under the conditions recommended by the manufacturer. Thiostrepton was obtained from the Squibb Institute for Medical Research (Kalamazoo, Mich.). Other biochemicals were purchased from commercial sources.

Cloning and Selection of Transformants

Cloning was carried out as described by Hopwood et al., 1985, supra, and Kendall and Kullum 1984, *Gene* 29:315–321. Lignin peroxidase negatives *S. lividans* TK64 was used as the recipient, while *S. viridosporus* T7A was the lignin peroxidase gene donor. The tyrosinase gene of pIJ702 was insertionally inactivated by incorporation of donor DNA fragments into pIJ702 during preparation of the *S. viridosporus* DNA library. BglII was used to cleave both chromosomal donor DNA (37° C.; 1 h) and pIJ702 (37° C.; 2 h). The single BGlII site in pIJ702 is located within the tyrosinase gene. BglII-digested donor DNA was fractionated on a sucrose gradient, and 5–10 Kb fragments were ligated into dephosphorylated (alkaline phosphatase for 1 h at 37° C.) pIJ702 using T4 ligase (16° C., overnight). The DNA library in pIJ702 was then transformed into protoplasts of *S. lividans* TK64 in soft agar containing polyethylene glycol (PEG). Transformed protoplasts were regenerated on the R2YE regeneration medium of Hopwood et al., 1985, supra. After 18–22 hours incubation of the R2YE medium at 30° C., the agar medium was overlaid with LB soft agar (Hopwood et al., 1985, supra containing thiostrepton (500 µg/ml). Thiostrepton resistant (tsr$^r$) colonies not expressing tyrosinase (mel$^-$) were considered to be expressing pIJ702 containing donor DNA inserts.

Screening for Lignin Peroxidase-Expressing Clones

Tsr$^r$/Mel$^-$ colonies from the R2YE medium were transferred to an agar medium containing nitrogen-free mineral salts (Borgmeyer and Crawford 1985, supra), carboxymethyl cellulose (10.0 g L$^{-1}$), yeast extract (10.0 g L$^{-1}$), casamino acids (0.25 g L$^{-1}$), thiostrepton (50 µg Ml$^{-1}$), and the blue polymeric dye Poly B-411 (0.2 g L$^{-1}$) (Sigma Chem. Co.). The dye is a substrate for ligninases (Sutherland, *Abstr. Ann. Meeting Amer. Soc. for Microbiol.*, 1985, p. 267). Upon oxidation by lignin peroxidase, the dye is decolorized. Transformants producing colonies with clear halos were picked as tentative lignin peroxidase clones.

Transformation of *S. lividans* with pIJ702/TK64.1

The transformation-regeneration procedure described above was also used to transform protoplasts of *S. lividans* strains TK64, TK23, and TK24 with 9.8 kb plasmid pIJ702/TK64.1, which was purified from lignin peroxidase expressing cells of recombinant *S. lividans* pIJ702/TK64.1 isolated during the present study. Colonies growing on the regeneration medium were transferred to Poly B-411 dye agar plates. After growth for 3–5 days on this medium at 30° C., colonies were examined for clear zones indicative of lignin peroxidase-catalyzed oxidation and decolorization of the Poly B-411.

Lignin Peroxidase Assay

Lignin peroxidase activity was routinely assayed with 2,4-dichlorophenol (2,4-DCP) (Sigma) as substrate (Ramachandra et al., 1988, supra). A final volume of 1.0 ml of the reaction mixture contained 200 µl of 100 mM sodium succinate buffer (pH 5.5), 100 µl of 82 mM 4-aminoantipyrine (Sigma), 100 µl of 1.0 mM 2,4-DCP, 100 µl of 4.0 mM hydrogen peroxide, 200 µl of the enzyme preparation, and 300 µl of water. The reaction was initiated by addition of hydrogen peroxide, and the increase in $A_{510}$ was monitored for 2 min at 37° C. One unit of enzyme activity was expressed as the amount of enzyme required for an increase in absorbance of 1.0 U min$^{-1}$. Activity could also be measured with L-3,4-dihydroxyphenylalanine (L-DOPA) (Sigma) as substrate (Ramachandra et al., 1987, supra).

Measurement of Extracellular Peroxide Production

Hydrogen peroxide concentrations in culture filtrates were measured by the method of Frew et al. 1983, *Anal. Chem. Acta* 155:139–150. At different time intervals, a known volume of filtrate (100 µl) from cultures of *S. viridosporus* T7A or *S. lividans* TK64, grown for 3–7 days in Poly B-411 liquid medium, was added without the dye, to 4-aminoantipyrine-phenol reagent (Frew et al., 1983, supra) also containing horseradish peroxidase (Sigma). The $A_{505}$ of the resulting solution was measured over time at 25° C. Hydrogen peroxide content was correlated with the $A_{505}$ value, or it could be calculated exactly from a standard curve.

Nondenaturing Polyacrylamide Gel Staining Assays

Extracellular proteins were analyzed by nondenaturing, discontinuous polyacrylamide gel electrophoresis (PAGE) on vertical slab gels (7.5% polyacrylamide) (Ramachandra et al., 1987, supra). After electrophoresis, proteins were visualized by silver staining (Hames and Rickwood, 1981, *Gel Electroporesis of Proteins: A Practical Approach* IRL Press, Oxford). Peroxidase bands on nondenaturing PAGE gels were developed by activity staining as previously described (Ramachandra et al., 1987, supra; Ramachandra et al., 1988, supra.

Growth of Streptomyces and Production of Lignin Peroxidase Using Lignocellulose as Substrate in Solid State Culture

*S. viridosporus* T7A, *S. lividans* TK64, and *S. lividans* TK64.1 were grown on 5 gram amounts of ground, extracted corn stover lignocellulose as previously described (CRawford et al., 1983, *Appl. Environ. Microbiol.* 45:898–904). In one experiment lignin peroxidase was also produced by *S. viridosporus* T7A in a liquid medium devoid of lignocellulose and consisting of nitrogen-free mineral salts supplemented with yeast extract (Ramachandra et al., 1987, supra).

RESULTS

Purified lignin peroxidase ALiP-P3, from *S. viridosporus* T7A in the presence of $H_2O_2$ as cosubstrate, will decolorize the blue dye Poly B-411. The reaction is reversible, and when it is carried out by placing the enzyme and peroxide together in wells cut in the center of Poly B-411 agar plates, an expanding clear halo appears in the blue agar as the enzyme and peroxide diffuse outward. *S. viridosporus* colonies also decolorize the dye, but the decolorization is more complete and permanent, an indication that enzymes in addition to ALiP-P3 are involved in oxidizing Poly B-411. Colonies of *S. lividans* TK64 do not decolorize the dye, although the colonies adsorb some dye. No clear halos appears around TK64 colonies during growth on the Poly B-411 medium. Based on these observations, a Poly B-411 decolorization colony screening assay was utilized for selection of lignin peroxidase-expressing clones of *S. lividans*.

Expression of lignin peroxidase by *S. lividans* transformants requires the presence of extracellular $H_2O_2$ cosubstrate. *S. lividans* TK64 produces $H_2O_2$ extracellularly in amounts similar to that excreted by *S. viridosporus* T7A when growing in the liquid Poly B-411 medium lacking dye or agar. In addition, *S. lividans* strains produce an extracellular enzyme activity which generates peroxide from various organic substrates. These results indicated that extracellular peroxide concentrations are adequate to supply lignin peroxidase-expressing clones with co-substrate.

Approximately 1000 melanin negative *S. lividans* TK64 colonies growing on thiostrepton-amended R2YE regeneration medium (presumed to contain *S. viridosporus* T7A DNA inserts in pIJ702) were picked and transferred to Poly B-411 agar medium plates. Of these clones, two cleared the dye after 3-5 days growth at 30° C. Colonies of these clones produced the same expanding clear halo as observed with pure enzyme. One clone, *S. lividans* pIJ702/TK64.1, was selected for further characterization, since it grew quickly and sporulated better on agar media than did the other clone.

Tentatively identified lignin peroxidase-expressing recombinant *S. lividans* TK64.1 was grown in solid state culture on 5 grams of extracted, ground corn stover lignocellulose (Crawford et al. 1983, supra) for 2 weeks at 30° C. and then tested for production of extracellular lignin peroxidase. As a positive lignin peroxidase production control, *S. viridosporus* T7A was grown similarly, but grown at 37° C., while as a negative control, plasmidless *S. lividans* TK64 was grown similarly. After 2 weeks, cultures were harvested by extraction with 50 ml of 0.1M phosphate buffer (pH 7.0) and filtration through glass wool. The aqueous filtrates were concentrated 3-fold by dialysis against polyethelene glycol (MW 15,000-20,000) and then assayed for lignin peroxidase activity by the nondenaturing PAGE gel activity staining assay and using the 2,4-DCP oxidation assay. The substrate used to detect peroxidase bands in the gels was L-Dopa (L-3,4-dihydroxyphenylalanine). In the presence of hydrogen peroxide, lignin peroxidase ALip-P3 *S. viridosporus* readily oxidizes this substrate, which results in an intense reddish brown color when the reaction is carried out in the presence of 4-aminoantipyrine (Ramachandra et al., 1987, supra).

*S. viridosporus* filtrates from mineral salts-yeast extract broth-grown cells contained a peroxidase-active band corresponding to the ALip-P3 lignin peroxidase band (Ramachandra et al., 1988 supra). *S. viridosporus* filtrates from the solid state lignocellulose culture contained significantly greater amounts of the lignin peroxidase and lesser amounts of other L-Dopa-oxidizing peroxidase bands, as has also been observed previously (Ramachandra et al., 1987 supra).

Solid state fermentation filtrates from the plasmidless *S. lividans* TK64 contained small smounts of several peroxidase active proteins, providing a low background level of peroxidase activity. This activity is not lignin peroxidase, though its presence complicates interpretation of data.

Solid state growth filtrates from *S. lividans* TK64.1 contained very high levels of peroxidase, and an intensely active band corresponded to the ALip-P3 band observed in *S. viridosporus* filtrates. Therefore, the PAGE gel assays support the conclusion that the cloned DNA codes for *S. viridosporus* T7A lignin peroxidase. This conclusion is also supported by the 4-DCP assay results.

Dialysis concentrated filtrates from *S. viridosporus* T7A, *S. lividans* TK64, and *S. lividans* TK64.1 showed 2,4-DCP oxidation activities of 0.10, 0.02, and 0.11 units $ml^{-1}$, respectively. In this experiment, the filtrates were from shake flask cultures grown for 4 days at 30° C. (37° C. for strain T7A) in the liquid mineral salts-yeast extract (0.6% w/v) supplemented with (0.05% w/v) of lignocellulose. For similar 4 day filtrates from a medium supplemented with carboxymethyl-cellulose (0.05% w/v) instead of lignocellulose, the corresponding values were 0.06, 0.03, and 0.07, respectively.

The plasmid encoding the ALip-P3 gene (pIJ702.LP) was purified from cells of *S. lividans* and characterized by restriction analysis. The plasmid contained a DNA insert of approximately 4 kb and the insert could be excised from pIJ702 with BglII. When the insert was purified, biotinylated, and used to probe *S. viridosporus* genomic DNA that had been restricted with BglII, the probe hybridized with genomic DNA fragments of approximately 4 kb size. These data confirm that the cloned gene originated from the *S. viridosporus* genome.

Purified pIJ702.LP was also used to transform *S. lividans* strains TK64, TK23, and TK24. In these transformations the frequencies of transformation varied, but all transformants expressing pIJ702.LP decolorized Poly B-411 when grown on the dye-containing medium. These results further confirm that the cloned peroxidase gene is responsible for the observed dye decolorization. One TK23 transformant, TK23.1/pIJ702.LP, was retained for further study.

*S. lividans* TK64 causes little lignocellulose weight loss when grown on corn stover lignocellulose in solid state cultures (S. Eaton, M.S. thesis, Univ. Idaho, 1987). In comparison, *S. viridosporus* T7A grows vigorously and causes substantial weight loss and loss of both lignin and carbohydrate components of the substrate (Crawford et al., 1983 supra). In a preliminary study, the ability of strain TK23 and recombinant strain TK23.1 to utilize corn stover lignocellulose was compared. Incubations were as solid state cultures. After 2 weeks of growth at 30° C., the lignocellulose weight loss resulting from growth of the Streptomyces was determined gravimetrically (Crawford et al. 1983 supra). Strains TK23 and TK23.1 generated weight losses of 3.3% and 6.2%, respectively. Uninoculated controls typically show a weight loss of about 3-4%. These data indicate that along with the lignin peroxidase gene of *S. viridos-* porus, the recombinant obtained the ability to at least partially decompose lignocellulose.

It is evident from the above results that the capability of transferring the ability to produce lignin peroxidase has been developed. Thus, by employing the subject constructs, one can greatly enhance the lignin peroxidase capability and production of homologous or heterologous hosts, one can produce the enzyme for treatment of lignin extracellularly, or use the enzyme as a catalytic oxidase.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated and purified DNA fragment consisting essentially of a region encoding an actinomycete lignin peroxidase.

2. A DNA fragment according to claim 1, wherein said DNA fragment is a DNA sequence of Streptomyces.

3. A DNA sequence according to claim 2, wherein said Streptomyces is S. viridosporus.

4. A DNA fragment according to claim 1, wherein said DNA fragment comprises the natural promoter region of said lignin peroxidase.

5. A vector comprising a replication system functional in an actinomycete host and a recombinant DNA sequence encoding an actinomycete lignin peroxidase.

6. A vector according to claim 5, wherein said DNA sequence is a sequence of Streptomyces.

7. A vector according to claim 6, wherein said Streptomyces is S. viridosporus.

8. A vector according to claim 5, wherein said DNA sequence comprises the natural promoter region of said lignin peroxidase.

9. A transformed actinomycete host comprising the vector of claim 5, wherein said recombinant DNA sequence encoding said actinomycete lignin peroxidase further comprises, in operable linkage with said lignin peroxidase-encoding DNA sequence, 5'-flanking transcriptional and translational regulatory DNA sequence elements and a 3'-flanking transcription termination region, said regulatory DNA sequence elements and said termination region functional in said host.

10. A transformed actinomycete host according to claim 10, wherein said DNA sequence comprises a portion of a stable extrachromosomal element.

11. A transformed actinomycete host according to claim 10, wherein said DNA sequence is a sequence of Streptomyces.

12. A transformed actinomycete host according to claim 10, wherein said Streptomyces is S. viridosporus.

13. A transformed actinomycete host according to claim 10, wherein said DNA sequence comprises the natural promoter region of said lignin peroxidase.

14. A transformed, non-actinomycete prokaryotic host comprising a recombinant DNA sequence encoding an actinomycete lignin peroxidase gene comprising a sequence encoding said lignin peroxidase under the transcriptional and translational control of a promoter and a termination region function in said host.

15. A method for producing a lignin peroxidase which comprises:
growing in an appropriate nutrient medium a transformed prokaryotic host according to claim 14; whereby said lignin peroxidase is produced.

16. A transformed actinomycete host comprising as a result of transformation a recombinant DNA sequence encoding a heterologous actinomycete lignin peroxidase gene comprising a sequence encoding said lignin peroxidase under the transcriptional and translational control of a promoter and a termination region functional in said host.

* * * * *